United States Patent [19]

DeSantis

[11] Patent Number: 5,502,052
[45] Date of Patent: Mar. 26, 1996

[54] USE OF A COMBINATION OF APRACLONIDINE AND TIMOLOL TO CONTROL INTRAOCULAR PRESSURE

[75] Inventor: Louis M. DeSantis, Fort Worth, Tex.

[73] Assignee: Alcon Laboratories, Inc., Fort Worth, Tex.

[21] Appl. No.: 364,831

[22] Filed: Dec. 22, 1994

Related U.S. Application Data

[63] Continuation of Ser. No. 812,889, Dec. 20, 1991, abandoned, which is a continuation of Ser. No. 472,686, Jan. 31, 1990, abandoned, which is a continuation of Ser. No. 186,504, Apr. 26, 1988, abandoned.

[51] Int. Cl.$^6$ .................... A61K 31/535; A61K 31/415
[52] U.S. Cl. .................... 514/236.2; 514/392; 514/913
[58] Field of Search .................... 514/236.2, 392, 514/913

[56] References Cited

U.S. PATENT DOCUMENTS

| | | | |
|---|---|---|---|
| 3,468,887 | 9/1969 | Stahle et al. | 548/315 |
| 3,852,468 | 12/1974 | Howe et al. | |
| 4,402,974 | 9/1983 | Matier et al. | 514/913 |
| 4,428,883 | 1/1984 | Hussein | 514/653 |
| 4,454,154 | 6/1984 | Matier | 514/913 |
| 4,455,317 | 6/1984 | Matier | 514/913 |
| 4,461,904 | 7/1984 | York | |
| 4,515,800 | 5/1985 | Cavero et al. | 514/913 |
| 4,517,199 | 5/1985 | York | 514/392 |
| 4,559,359 | 12/1985 | Matier | 514/913 |
| 4,578,403 | 3/1986 | Matier | 514/913 |
| 4,581,376 | 4/1986 | Macri | 514/913 |
| 4,734,438 | 3/1988 | Macri | 514/913 |

FOREIGN PATENT DOCUMENTS

| | | |
|---|---|---|
| 0286903 | 10/1988 | European Pat. Off. |
| WO87/07141 | 12/1987 | WIPO |

OTHER PUBLICATIONS

AMA Drug evaluation, 2nd, 1973, pp. 675–686.

Sugar, The Ten Commandments for Management of Primary Open Angle Glaucoma–Sugar–Glaucoma 1(1)–1979–pp. 9–15 (1979).

Rouot, et al. "Clonidine and Related Analogues. Quantitative Correlations" *J. Med. Chem.*, vol. 19, pp. 1049–1054 (1976).

Evans et al. "B–Adrenergic Receptor Blockers as Therapeutic Agents" *Ann. Reports in Med. Chem.*, vol. 14, pp. 81–87 (1979).

Timmermans et al. "Structure–Activity Relationships in Clonidine–Like Imidazolidines and Related Compounds" *Gustav Fischer Verlag* (1980).

Schwartz, B., "Method of Treating Glaucoma with Corticosteroids and Adrenergic Drugs", *Chemical Abstract*, vol. 109, No. 7, issued 15 Aug. 1988, p. 76.

Machin et al. "B$_1$ Selective Adrenoceptor Antagonists, 2,4–Ether–Linked Phenoxypropanolamines" *J. Med. Chem.*, vol. 26, pp. 1570–1575 (1983).

Machin et al. "B$_1$ Selective Adrenoceptor Antagonists, 3,4–Azolyl–Linked Phenoxypropanolamines" *J. Med. Chem.*, vol. 27, pp. 503–509 (1984).

Pitha et al. "B–Adrenergic Antagonists with Multiple Pharmacophores: Persistent Blockade of Receptors" *J. Med. Chem.*, vol. 26, pp. 7–11 (1983).

Kierstead et al., "B$_1$ Selective Adrenoceptor Antagonists. 1, Synthesis and B–Adrenergic Blocking Activity of a Series of Binary (Aryloxy) Propanolamines" *J. Med. Chem.*, vol. 26, pp. 1561–1569 (1983).

Erhardt et al. "Ultra–Short–Acting B–Adrenergic Receptor Blocking Agents. 3. Ethylenediamine Derivatives of (Aryloxy) Propanolamines Having Esters on the Aryl Function" *J. Med. Chem.*, vol. 26, pp. 1109–1112 (1983).

Baldwin et al. "B$_1$ Selective Adrenoceptor Antagonists: Examples of the 2–4–3–(Substituted–amino)–2–hydroxypropoxy phenyl imidazole Class" *J. Med. Chem.*, vol. 26, pp. 649–657 (1983).

McClure et al. "Antihypertensive B–Adrenergic Blocking Agents: N–Aralkyl Analogues of 2–3–(tert–Butylamino)–2–hydroxypropoxy–3–cyanopyridine" *J. Med. Chem.*, vol. 26, pp. 649–657 (1983).

Large et al. "B–Adrenergic Blocking Agents. 23,1–(Substituted–amido) phenoxy–3–(substituted–amino) alkyl amino propan–2–ols" *J. Med. Chem.*, vol. 26, pp. 352–357 (1983).

Allen, et al., "Additive Effect of Betaxolol and Epinephrine in Primary Open Angle Glaucoma", *Archives of Ophthalmology*, vol. 104, No. 7, Jul. 1986, pp. 1178–1184.

Leydhecker, W., "Augenheilkunde", 23rd Edition, Springer Verlag, pp. 165–171 (1987).

Schnarr, et al., "Wirksamkeit und Vertäglichkeit Wirkstoffkombination von Timolol und Pilocarpin–Eine Pilostudie", *Klin. Monatsbl. Augenheilk*, 191(6), pp. 436–438 (1987).

Mehrotra, et al., "Compaative Evaluation of Pilocarpine 2% and combined Guanethidine 1% & Adrenaline 0.5% in the treatment of Chronic simple Glaucoma", *Ind. J. Ophthal.*, vol. 35, No. 3, pp. 146–148 (1987).

Morrison, et al., "Adjunctive Glaucoma Therapy: A Comparison of Apraclonidine to Dipivefrin when Added to Timolol Maleate", *Ophthalmology*, vol. 96, No. 1, pp. 3–7 (1989).

Yaldo, et al. "Additive Effect of 1% Apraclonidine Hydrochroride to Nonselective β–Blcokers", *Ophthalmology*, vol. 98, No. 7, pp. 1075–1078 (1991).

West, et al., "Therapeutic Response Interactions Between Timolol Maleate and Dipivefrin Hydrochloride", *Australian and New Zealand Journal of Ophthalmology*, vol. 15, pp. 131–134 (1987).

(List continued on next page.)

*Primary Examiner*—Zohreh Fay
*Attorney, Agent, or Firm*—James A. Arno; Gregg C. Brown

[57] ABSTRACT

Ophthalmic pharmaceutical compositions useful in controlling elevated intraocular pressure associated with glaucoma and other ophthalmic conditions are described. A method of controlling elevated intraocular pressure with those compositions is also described. The compositions contain a combination of an alpha-2 agonist (e.g., para-amino clonidine) and a beta blocker (e.g., betaxolol).

1 Claim, No Drawings

OTHER PUBLICATIONS

Burke, et al., "The Ocular Effects of Xylazine in Rabbits, Cats and Monkeys", *Journal of Ocular Pharmacology*, vol. 2, No. 1, pp. 9–20 (1986).

Stiegler, G., "Bupranolol–augentropfen (Ophtorenin®) in der Glaukom–Dauertherapie", *Klin. Mbl. Augenheilk*, 174, pp. 267–275 (1979) (including English translation).

Bunin, et al., "Modern Preparations for Treatment of Glaucoma (Review)", *Khim. Farm.*, 2h. 21, No. 11 pp. 1395–1405 (1987) (including English translation).

Rompp Chemie Lexikon, p. 4406.

Keates, et al., "Safety and Effectiveness of Concomitant Administration of Dipivefrin and Timolol Maleate", *American Journal of Ophthalmology*, vol. 91, pp. 243–248 (1981).

Brown, et al., "ALO 2145 Reduces the Intraocular Pressure Elevation after Anterior Segment Laser Surgery", *Ophthalmology*, vol. 95, No. 3, pp. 378–384 (1988).

The 1986 Red Lists.

Nielsen, "TIMOLOL Hypotensive Effect, Used Alone and in Cmobination for Treatment of Increased Intraocular Pressure", *Acta Ophthalmologica*, vol. 56, pp. 504–509 (1978).

Fechner, Medikametöse Augentherapie.

USE OF A COMBINATION OF APRACLONIDINE AND TIMOLOL TO CONTROL INTRAOCULAR PRESSURE

This is a continuation, of application Ser. No. 07/812,889, filed Dec. 20, 1991, now abandoned, which is a continuation of application Ser. No. 07/472,686, filed Jan. 31, 1990, (now abandoned), which is a continuation of application Ser. No. 07/186,504, filed Apr. 26, 1988, (now abandoned).

BACKGROUND OF THE INVENTION

1. Field of the Invention

The present invention relates to the field of ophthalmology. More particularly, the invention relates to the treatment of glaucoma and associated elevations of intraocular pressure, and to the treatment of ocular hypertension associated with other diseases or conditions. The invention is directed to providing topical, ophthalmic, pharmaceutical compositions which include, as principal active ingredients, combinations of one or more alpha-2 agonists, such as clonidine derivatives (e.g., para-amino clonidine) and one or more beta-blockers (e.g., betaxolol).

2. Discussion of Related Art

The underlying causes of glaucoma are not fully understood. The symptomatology of this disease includes elevated pressure levels within the eye. These pressure elevations may be caused by either over production of fluid within the eye, or inadequate outflow of fluid from the eye. The intraocular fluid is referred to as "aqueous humor." The internal pressure of the eye associated with the amount of fluid inside the eye is referred to as "intraocular pressure" or "IOP." Although the causes of glaucoma and associated elevations of intraocular pressure are not fully understood, the prognosis of untreated or inadequately treated glaucoma is known to include very serious ocular manifestations, namely blindness or significant loss of vision. Thus, there is a continuing need for therapies which control the elevated intraocular pressure associated with glaucoma.

A significant number of glaucoma patients are required to administer more than one drug in order to achieve therapeutic control of their intraocular pressure. In other words, a single drug does not provide adequate control of intraocular pressure in these patients. The drugs currently utilized in the treatment of glaucoma include miotics (e.g., pilocarpine, carbachol, and acetylcholinesterase inhibitors), sympathomimetics (e.g., epinephrine and dipivalylepinephrine), beta-blockers (e.g., betaxolol, levobunolol and timolol), alpha-2 agonists (e.g., para-amino clonidine) and carbonic anhydrase inhibitors (e.g., acetazolamide, methazolamide and ethoxzolamide). Miotics and sympathomimetics are believed to lower intraocular pressure by increasing the outflow of aqueous humor, while beta-blockers, alpha-2 agonists and carbonic anhydrase inhibitors are believed to lower intraocular pressure by decreasing the formation of aqueous humor. All five types of drugs have potential side effects. Miotics, such as pilocarpine, can cause blurring of vision and other visual side effects which may either decrease patient compliance or require termination of miotic drug therapy. Carbonic anhydrase inhibitors can also cause serious side effects which affect patient compliance and/or necessitate withdrawal of the drug therapy. At least one beta-blocker, timolol, has increasingly become associated with serious pulmonary side effects attributable to its effect on beta-2 receptors in pulmonary tissue. In addition to these side effects, a therapy regimen which includes the use of two or more pharmaceutical compositions containing drugs selected from two or more of the above-cited classes requires the patient to apply the compositions to the affected eye(s) in separate, spaced dosages, several times per day. Patient compliance with such complicated dosage regimens can be very poor, particularly in elderly patients. Since the majority of glaucoma patients are elderly, this patient compliance problem is significant.

In light of the foregoing circumstances, it is clear that a need exists for new, more potent antiglaucoma compositions which avoid or reduce the above-cited side effects and enhance patient compliance. The present invention is directed to the provision of such compositions.

SUMMARY OF THE INVENTION

The present invention is directed to the provision of antiglaucoma compositions which comprise a combination of one or more alpha-2 agonists and one or more beta-blockers. The invention is also directed to methods of controlling intraocular pressure utilizing those compositions.

Compounds having alpha-2 agonist activity are known to lower intraocular pressure. For example, the substituted 2-(arylimino) imidazolidines described in U.S. Pat. Nos. 4,461,904; 4,515,800; and 4,517,199 are known to lower intraocular pressure. The entire contents of those patents are hereby incorporated in the present specification by reference. The mechanisms by which alpha-2 agonists lower intraocular pressure are not fully understood. It is believed, however, that these agents reduce intraocular pressure by suppressing the inflow of aqueous humor.

Beta-blockers, such as timolol and betaxolol, are also known to lower intraocular pressure, and have been utilized for that purpose for several years. The biological mechanism by which beta-blockers lower intraocular pressure is not entirely clear. It is believed that these compounds control intraocular pressure by decreasing the production of aqueous humor in the ciliary processes of the eye.

As mentioned above, two or more different types of drugs are sometimes required to achieve therapeutic control of intraocular pressure. The present invention is directed to the provision of topical, ophthalmic, pharmaceutical compositions containing two different types of active ingredients which together achieve a greater reduction in intraocular pressure than that achievable with the same concentration of either ingredient used alone. The mechanisms by which the combinations of the present invention achieve such reductions of intraocular pressure are not completely understood. In general, it is believed that the alpha-2 agonists and beta blockers utilized in the present compositions reduce the inflow of aqueous humor by means of complementary mechanisms of action. While applicant does not wish to be bound by any theory, it is postulated that beta blockers inhibit the formation of aqueous humor in the ciliary processes by binding with beta-2 receptors, thereby preventing the receptors from being stimulated to form aqueous humor; while alpha-2 agonists appear to act by means of a three part mechanism involving: (1) vasoconstriction in the ciliary processes, (2) binding with presynaptic alpha-2 receptors to inhibit the release of neurotransmitters that act on beta-2 receptors to cause aqueous humor formation, and (3) binding with inhibitory alpha-2 receptors in ciliary epithelial cells thereby preventing aqueous humor formation. Whatever the mechanism, it is clear that the present combinations have a potent and surprising IOP lowering effect.

DETAILED DESCRIPTION OF THE INVENTION

The antiglaucoma compositions of the present invention comprise a combination of a therapeutically effective amount of one or more alpha-2 agonists and a therapeutically effective amount of one or more beta-blockers. The ratio of the alpha-2 agonist component to the beta-blocker component may vary considerably depending on the relative potency of the specific components utilized and other factors, such as the degree of intraocular pressure reduction desired and the nature of the condition being treated, The ratio of the components employed is therefore left to the discretion of skilled clinicians, The ratio on a percent by weight concentration basis will typically be in the range of about 0.1:10 to 10:0.1 alpha-2 agonist:beta-blocker.

The alpha-2 agonists which can be employed in the compositions of the present invention include all pharmaceutically acceptable compounds which have alpha-2 agonist activity and are effective in controlling intraocular pressure, Preferred alpha-2 agonists include clonidine, a substituted 2-(arylimino) imidazolidine, and derivatives thereof, including the compounds described in the three U.S. patents cited above and incorporated herein by reference. A preferred group or class of clonidine derivatives are trisubstituted 2-(phenylimino) imidazolidines of formula:

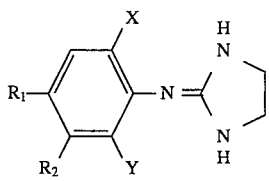

wherein: $R_1$ and $R_2$ are selected from H, OH, NHR' and

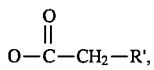

with R' being selected from H and $C_1$–$C_4$ alkyl, provided that one of $R_1$ and $R_2$ is hydrogen; and X and Y are selected from Br, Cl, $CH_3$ and $CH_2CH_3$. Specific examples of compounds from this group are set forth in Table 1 below:

TABLE 1

| Compound | $R_1$ | $R_2$ | X | Y |
|---|---|---|---|---|
| 1 | $NHCH_3$ | H | $CH_3$ | $CH_3$ |
| 2 | $NHCH_3$ | H | $CH_2CH_3$ | $CH_2CH_3$ |
| 3 | $NHCH_3$ | H | Cl | Cl |
| 4 | $NH_2$ | H | Br | Br |

A group of especially preferred clonidine derivatives of formula (I) are those in which $R_1$ and $R_2$ are selected from H and $NH_2$, provided that one of $R_1$ and $R_2$ is H, and X and Y are selected from Cl, $CH_3$, and $CH_2CH_3$. Specific examples of compounds from this group are set forth in Table 2 below:

TABLE 2

| Compound | $R_1$ | $R_2$ | X | Y |
|---|---|---|---|---|
| 5 | H | $NH_2$ | $CH_3$ | $CH_3$ |
| 6 | $NH_2$ | H | $CH_2CH_3$ | $CH_2CH_3$ |
| 7 | H | $NH_2$ | Cl | Cl |
| 8 | $NH_2$ | N | $CH_2CH_3$ | Cl |
| 9 | $NH_2$ | H | $CH_3$ | Cl |
| 10 | $NH_2$ | H | $CH_3CH_3$ | $CH_3$ |
| 11 | $NH_2$ | H | $CH_3$ | $CH_3$ |
| 12 | H | $NH_2$ | $CH_2CH_3$ | $CH_2CH_3$ |
| 13 | $NH_2$ | H | Cl | Cl |

Of these specific examples, p-amino clonidine (i.e., Compound 13) has been found to be particularly well-suited for use in the present invention.

Another preferred group of clonidine derivatives are those wherein $R_1$ and $R_2$ are both H and X and Y are selected from Br, Cl, $CH_3$ and $CH_2CH_3$. Clonidine (X and Y=Cl) is included in this group. Among this group, compounds wherein at least one of X and Y is alkyl are particularly preferred. Compounds of this type are described, for example, in U.S. Pat. No. 3,468,887, and *J. Med. Chem.*, Vol. 19, pages 1040–54 (1976); the contents of these publications relating to the structure, preparation and physical properties of clonidine derivatives, particularly substituted 2-(arylimino) imidazolidines, are incorporated herein by reference. Specific examples of compounds from this group are set forth in Table 3 below:

TABLE 3

| Compound | $R_1$ | $R_2$ | X | Y |
|---|---|---|---|---|
| 14 | H | H | $CH_2CH_3$ | $CH_2CH_3$ |
| 15 | H | H | $CH_2CH_3$ | $CH_3$ |
| 16 | H | H | Cl | $CH_2CH_3$ |
| 17 | H | H | Cl | Cl |

In addition to the 2-(arylimino) imidazolidines identified above, other groups or classes of alpha-2 agonists which may be utilized in the present invention include 2-(arylimino) oxazolidines; 2-(arylmethylene) imidazolidines; 2-(arylimino) pyrrolidines; arylalkylaminoguanidines, such as aryl-imidazoquinazolines and phenylacetylguanidines; and 2-(phenylimino) diazocyclopentenes. All of these groups of drugs may be referred to as being clonidine derivatives or "clonidine-like" drugs. A comprehensive discussion of the properties of clonidine and clonidine-like compounds is presented in a publication by Timmermans et al. titled "Structure-Activity Relationships in Clonidine-Like Imidazolidines and Related Compounds" (pages 1–97, published in 1980 by Gustav Fischer Verlag, of Stuttgart and New York). The entire contents of that publication are hereby incorporated in the present specification by reference. As indicated by Timmermans et al., the molecular structure of clonidine consists of three parts: an aromatic (i.e., aryl) portion, a bridge, and an imidazolidine moiety. Timmermans et al. disclose many compounds which have been produced by modifying one or two of these three parts, but which retain one of the three parts intact. For purposes of the present specification, all such compounds are defined as being "clonidine derivatives."

The antiglaucoma compositions of the present invention will typically contain one or more of the above-described alpha-2 agonists in an amount of about 0.02 to 2.0 percent by weight (wt. %).

The beta-blockers which may be utilized in the present invention include all pharmaceutically acceptable compounds which are capable of reducing the production of aqueous humor when applied topically to the eye. As utilized herein, the term "beta-blocker" means a compound which acts to block beta-1 and/or beta-2 receptors from stimulation by means of binding with those receptors, and has the ability to control intraocular pressure. Beta blockers may be generally identified by the following structure:

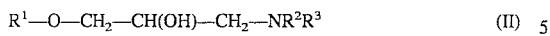

$$R^1—O—CH_2—CH(OH)—CH_2—NR^2R^3 \quad (II)$$

wherein: $R^1$ is a substituted or unsubstituted cyclic or aliphatic moiety; cyclic moieties include mono- and polycyclic structures which may contain one or more heteroatoms selected from C, N, and O; $R^2$ and $R^3$ are independently selected from H and substituted and unsubstituted alkyl. With regard to beta blockers of structure (II), above, the following references are incorporated herein by reference: *Annual Reports in Medicinal Chemistry* Vol. 14, pages 81–87 (1979); *J. Med. Chem.* Vol. 26, pages 1570–1576 (1983); ibid., Vol. 27, pages 503–509 (1984); ibid. Vol. 26, pages 7–11 (1983); ibid. Vol. 26, pages 1561–1569 (1983); ibid., Vol. 26, pages 1109–1112 (1983); ibid., Vol. 26, pages 950–957 (1983); ibid. Vol. 26, pages 649–657 (1983); and ibid., Vol. 26, pages 352–357 (1983).

Specific examples of beta blockers which may find use in the present invention include acebutolol, adimolol, alprenolol, atenulol, avotinolol, betaxolol, befunolol, bevantolol, bisoprolol, bopindolol, bucomolol, bupranolol, butidrine, bunitolol, bunolol, butocrolol, butoamine, carazolol, carteolol, celiprolol, cetamolol, cicloprolol, diacetolol, draquinolol, epanolol, esmolol, exaprolol, hepunolol, indenolol, iprocrolol, isoxaprolol, labetolol, levobunolol, mepindolol, metipranolol, metoprolol, moprolol, nadolol, nifenalol, oxprenolol, pamatolol, penbutolol, pindolol, practolol, procinolol, pronethalol, propranolol, SKF 95018, sotalol, tazolol, tienoxolol, timolol, tiprenolol, tolamolol, toliprolol, and xamoterol. The most preferred beta-blocker is betaxolol. Other preferred beta-blockers include timolol, levobunolol, carteolol, metipranolol, and pindolol. All of the foregoing compounds are known.

The antiglaucoma compositions of the present invention will typically contain one or more of the above-described beta-blockers in an amount of about 0.01 to 3.0 percent by weight (wt. %).

In addition to the above-described principal active ingredients, the antiglaucoma compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, ONAMER M and other agents equally well known to those skilled in the art. Such preservatives, if utilized, will typically be employed in an amount of from about 0.001% to 1.0% by weight (wt. %). Examples of suitable agents which may be utilized to adjust the tonicity or osmolality of the formulations include sodium chloride, potassium chloride, mannitol, dextrose glycerine and propylene glycol. Such agents, if utilized, will be employed in an amount of about 0.1% to 10.0% by weight (wt. %).

As will be appreciated by those:skilled in the art, the compositions may be formulated in various dosage forms suitable for topical ophthalmic delivery, including solutions, suspensions, emulsions, gels, and erodible solid ocular inserts. The compositions are preferably aqueous, and have a pH in the range of 3.5 to 8.0 and an osmolality in the range of 280 to 320 millimoles per liter (mm/l).

The following example further illustrates the antiglaucoma compositions of the present invention.

EXAMPLE

The following formulation is typical of aqueous ophthalmic solutions of the present invention.

| Ingredient | Amount (wt. %) |
|---|---|
| Para-amino clonidine | 0.1 |
| Betaxolol | 0.5 |
| Benzalkonium Chloride | 0.01 |
| Edetate Sodium | 0.05 |
| HCl and/or NAOH | QS pH 7.4 |
| Purified Water | QS 100 |

The present invention is also directed to methods of treating and controlling ocular hypertension associated with glaucoma and other ophthalmic diseases and abnormalities. The methods comprise topical application of a therapeutically effective amount of a composition according to the present invention to the affected eye(s) of the patient. The frequency and amount of the dosage will be determined by the clinician based on various clinical factors. The methods will typically comprise topical application of one to two drops (or an equivalent amount of a solid or semisolid dosage form) to the affected eye one to two times per day.

What is claimed is:

1. A method of controlling intraocular pressure which comprises applying topically to the affected eye a therapeutically effective amount of a composition comprising: 0.02 to 2.0 wt. % of para-amino clonidine or a pharmaceutically acceptable salt thereof, 0.01 to 3.0 wt. % of timolol or a pharmaceutically acceptable sale thereof, and a pharmaceutically acceptable vehicle therefor.

* * * * *

UNITED STATES PATENT AND TRADEMARK OFFICE
CERTIFICATE OF CORRECTION

PATENT NO. : 5,502,052
DATED : March 26, 1996
INVENTOR(S) : Louis M. DeSantis

It is certified that error appears in the above-identified patent and that said Letters Patent is hereby corrected as shown below:

Column 6, line 47, after the word "acceptable", please delete "sale" and substitute therefor —salt—.

Signed and Sealed this

Sixth Day of August, 1996

Attest:

BRUCE LEHMAN

Attesting Officer

Commissioner of Patents and Trademarks